United States Patent [19]

Ishiguro et al.

[11] Patent Number: 5,607,453
[45] Date of Patent: Mar. 4, 1997

[54] COMPOSITE MEDICAL TREATING DEVICE COMPOSED FERRODIELECTRIC SUBSTANCE AND SEMICONDUCTOR

[75] Inventors: Saburo Ishiguro, Tokyo; Tatsuo Inoue, Hiratsuka; Yoshitsugu Fujita, Koganei; Tetsuhiro Iwata, Iwaki, all of Japan

[73] Assignee: Furukawa Co., Ltd., Japan

[21] Appl. No.: 429,887

[22] Filed: Apr. 27, 1995

[30] Foreign Application Priority Data

Apr. 28, 1994 [JP] Japan .................................. 6-092021

[51] Int. Cl.$^6$ ...................................................... A61N 1/00
[52] U.S. Cl. .................. 607/2; 607/46; 607/145; 607/115
[58] Field of Search ............................ 607/1, 2, 46, 48, 607/50, 115, 145

[56] References Cited

U.S. PATENT DOCUMENTS

| | | |
|---|---|---|
| 4,047,214 | 9/1977 | Francombe et al. .................... 357/23 |
| 4,091,803 | 3/1978 | Pinder . |
| 4,163,447 | 8/1979 | Orr . |
| 4,233,987 | 11/1980 | Feingold . |
| 4,375,219 | 3/1983 | Schmid . |
| 4,402,326 | 9/1983 | Okano et al. . |
| 5,225,126 | 7/1993 | Alles et al. ................................ 264/63 |

FOREIGN PATENT DOCUMENTS

| | | |
|---|---|---|
| 0296248 | 12/1985 | European Pat. Off. . |
| 7609259 | 10/1977 | France . |
| 3437493 | 4/1986 | Germany . |
| 0229200 | 7/1987 | Germany . |
| 1240967 | 10/1986 | Japan ................................... 607/1 |
| 5337192 | 5/1993 | Japan . |

*Primary Examiner*—Jeffrey R. Jastrzab
*Attorney, Agent, or Firm*—Young & Basile, P.C.

[57] ABSTRACT

A composite medical treating device includes laminations of an n-type semiconductor film and a p-type semiconductor film coated on a surface of a ferrodielectric substance. When the composite medical treating device is affixed to a part of skin having a stiff portion and a pain, potentials of −, +, −, +, −, + are induced on a surface of the ferrodielectric substance in response to changes of potentials of +, −, +, −, + of the epidermis. Since the laminations of the n-type semiconductor film and the p-type semiconductor film are coated on the surface of the ferrodielectric substance, minus electricity is allowed to flow to the epidermis passing through the n-p laminations. However, plus electricity does not pass through the n-p (semiconductor) laminations and does not flow to the epidermis. Thus, the epidermis potential returns from plus to minus potential and is stabilized. When the epidermis potential returns from plus to minus potential and is stabilized, a dermis potential returns to plus due to the dielectric action, and since stimulus to a nerve is removed, pain is also removed.

8 Claims, 7 Drawing Sheets

COMPOSITE MEDICAL TREATING DEVICE COMPOSED FERRODIELECTRIC SUBSTANCE AND SEMICONDUCTOR

BACKGROUND OF THE INVENTION

1. Field of the Invention

The present invention relates to a medical treating device used for the medical treatment of muscular pain, stiff shoulders, and the like, and for activating muscle and skin, and for improving athletic ability.

2. Description of the Prior Art

For medical treatment of muscular pain, stiff shoulders, and the like, a semiconductor medial treating device is used which is formed of a semiconductor crystal, such as germanium, silicon, or the like, or by coating a thin semiconductor film on a molded product.

Figure 10:
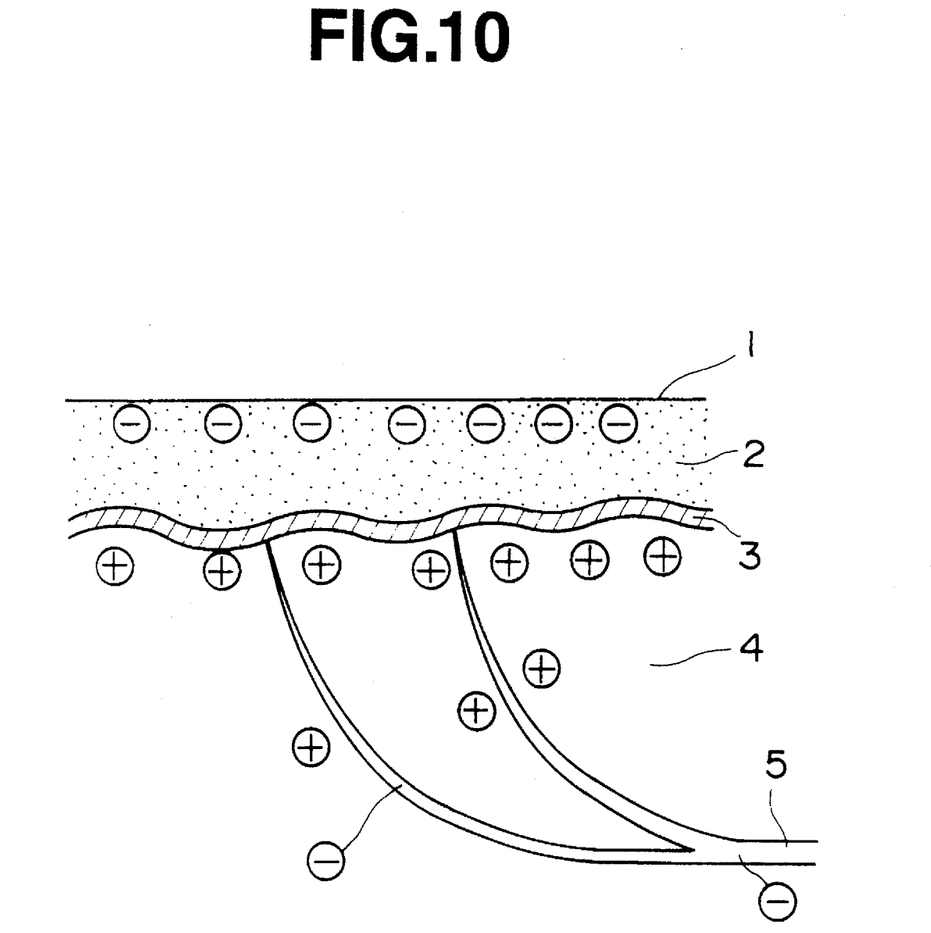
FIG. 10 is a diagram for explaining a state of potential in normal skin.

Normally, in human skin, when it is in a normal state, as shown in FIG. 10, a surface keratin layer 1 of an epidermis 2 is charged at −20 to −30 mv, and a dermis 4 sandwiching a basement membrane 3 between the dermis 4 and the epidermis 2 is charged at +2− to +30 mv. When a morbid state occurs in which the potential of the epidermis is inverted to plus (positive), and the potential of the dermis 4 is inverted to minus (negative), a stiff condition and pain are caused.

In a p-type semiconductor, since holes serve as carriers, the p-type semiconductor has properties in which the p-type semiconductor is charged to minus potential by absorbing electrons, and when the p-type semiconductor is affixed to a part having a stiff portion or a pain, it has the effect of making the potential of the skin surface minus, and to return the potential of the dermis to plus, so that the p-type semiconductor is considered effective as a medical treatment as described in Japanese Patent Laid-Open Publication Hei 5-337192.

Figure 5:
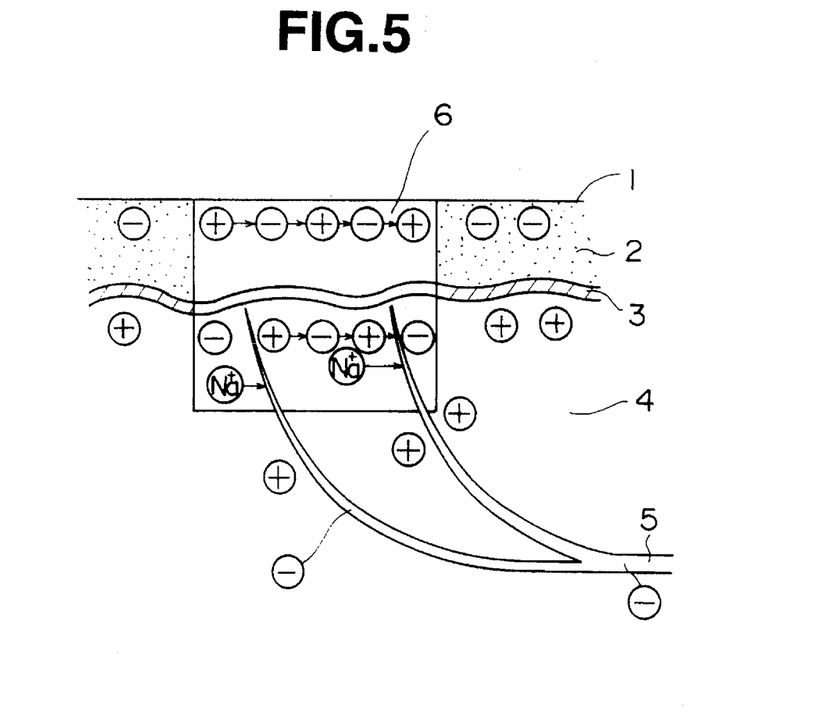
FIG. 5 is a diagram for explaining a state of potential in skin having a stiff portion and a pain.

However, according to the nervous physiology, the stiff portion and pain are not caused by only the mere inversion of potential. The plus charging of the dermis 4 side is due to a cell membrane potential of $Na^+$ ions or the like. Nerve and intracellular fluid contain less $Na^+$ ions so that they are charged to minus potential. Since the extracellular fluid contains $Na^+$ ions as much as ten times the quantity of $Na^+$ ions in the intracellular fluid, the extracellular fluid is charged to plus potential. When this state is changed to a morbid state so that a stiff portion and a pain are caused, as shown in FIG. 5, in a part 6 having a stiff portion and a pain, $Na^+$ ions flow into the inside of cells and a nerve 5, and this flow is transmitted as an impulse of cells, the inside of the cell temporarily charges to plus potential, and the outside of cells (dermis potential) becomes minus so that the potential is inverted. However, since a sodium pump is operated in the cycle of millisecond, the $Na^+$ ions are discharged from the inside of cells, and the inside of cells becomes again minus, and the outside of cells (dermis potential) returns to plus. The reason why pain continues is that the above-mentioned states are repeated and the potential of the dermis fluctuates between −, +, −, +. −, and so on, and in some cases, it takes time to stabilize the potential of the epidermis to minus by the action of only the minus potential of the p-type semiconductor, and thus, a sufficient effect cannot be obtained.

SUMMARY OF THE INVENTION

The present invention solves the problems in the above-mentioned semiconductor medical treating device, and it is an object of the present invention to provide a composite medical treating device composed of a ferrodielectric substance and a semiconductor which is capable of removing pains due to morbid fluctuations of skin potential.

In the present invention, the above-mentioned problems are solved by employing a structure in which laminations of an n-type semiconductor film and a p-type semiconductor film are coated on a surface of a ferrodielectric substance or a material containing the ferrodielectric substance.

As the material containing the ferrodielectric substance, woven textile, non-woven textile, paper, plastics, or ceramics to which a ferrodielectric substance powder is textile-blended, mixed, coated, or bonded is used.

As the ferrodielectric substance, titanium oxide, barium titanate, strontium titanate, lead titanate, lithium niobate, lithium tantalate, PZT, or rochelle salt is used.

As the n-type semiconductor film and the p-type semiconductor film, a thin film of silicon, germanium, gallium phosphide, indium phosphide, zinc selenide, zinc sulfide, or an organic semiconductor is used.

When a composite medical treating device 10 composed of a ferrodielectric substance and a semiconductor according to the present invention is affixed to a part 6 having a stiff portion and a pain in the skin, potentials of −, +, −, +, −, are induced in a surface of a ferrodielectric substance 7 corresponding to changes of epidermis potentials of +, −, +, −, +. Since laminations of an n-type semiconductor film 8 and a p-type semiconductor film 9 are coated on a surface of the ferrodielectric substance 7, minus electricity flows to an epidermis 2 through the n-p laminations (semiconductor junction) because of the properties of the semiconductor. However, plus electricity does not pass through the n-p laminations and does not flow to the epidermis 2. As a result, an epidermis potential S returns from plus to minus and is stabilized to minus. When the epidermis potential S returns to minus and is stabilized, a dermis potential C returns to plus due to a dielectric action, and since stimulus to a nerve 5 is removed, the pain is also removed. Ultimately, a stabilized state prevails and the part is released from stiffness and the pain. When the pain is removed, since the surface potential D of the ferrodielectric substance becomes plus and no minus potential is generated, the minus electricity does not flow excessively to the epidermis 2.

DESCRIPTION OF THE PREFERRED EMBODIMENTS

With reference to FIGS. 1 to 4, a composite treating device 10 includes a ferrodielectric substance 7 whose surface is coated with laminations of an n-type semiconductor film 8 and a p-type semiconductor film 9.

Figure 1:
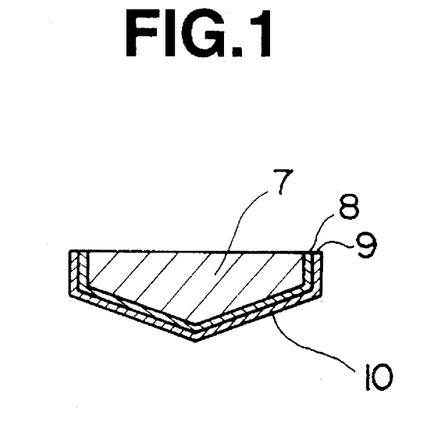
FIG. 1 is a longitudinal sectional view of a composite medical treating device composed of a ferrodielectric substance and a semiconductor in one embodiment of the present invention.
Figure 2:
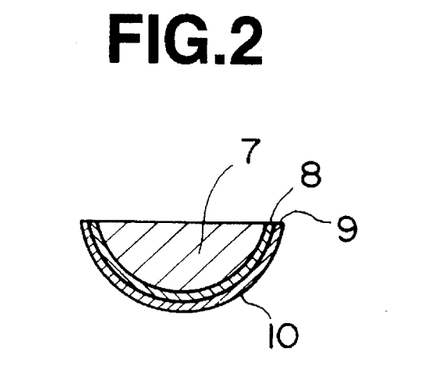
FIG. 2 is a longitudinal cross sectional view of a composite medical treating device in another embodiment of the present invention.

As the ferrodielectric substance 7, titanium oxide, barium titanate, strontium titanate, lead titanate, lithium niobate, lithium tantalate, PZT, or rochelle salt is used, and in embodiments in FIGS. 1 and 2, powders of such substances are sintered to form ceramics, or such powders are mixed with resin to form a molded product.

Figure 3:
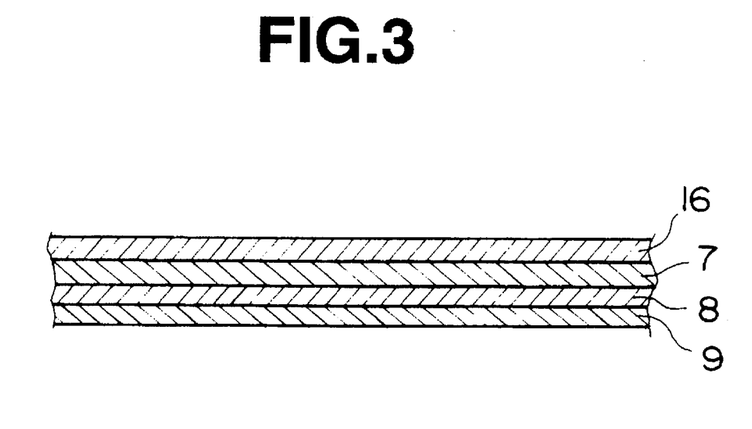
FIG. 3 is a longitudinal cross sectional view of a composite medical treating device in still another embodiment of the present invention.
Figure 4:
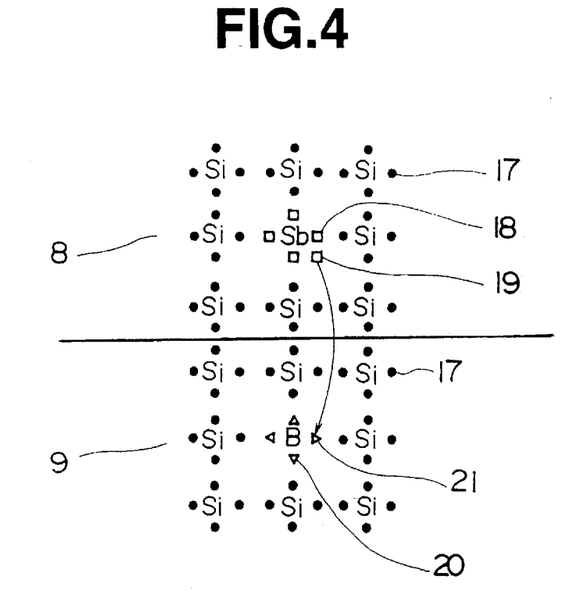
FIG. 4 is a diagram for explaining an example of a bonding state in a semiconductor.

In an embodiment shown in FIG. 3, a ferrodielectric substance 7 is coated on a cloth member 16, such as woven textile, non-woven textile, paper, plastics, or the like, and after drying of the coated cloth member 16, an n-type semiconductor film 8 and a p-type semiconductor film 9 are coated and laminated on the coated cloth member 16. The ferrodielectric substance 7 may be textile blended with a textile to form a woven textile.

The coating of the n-type semiconductor film 8 and the p-type semiconductor film 9 may be carried out by any method such as sputtering, CVD, and MOCVD coating. However, first, the n-type semiconductor film 9 is coated. The reason for this is to allow minus electricity to pass through among electricity induced in the ferrodielectric substance 7, and to prevent plus electricity from passing through. Since a spike potential of a nerve which is sensitive to pain vibrates to + and − in the cycle of a millisecond, a potential induced in the ferrodielectric substance 7 also varies in the cycle of a millisecond. Accordingly, the thickness of the n-type semiconductor film 8 and the p-type semiconductor film 9 which are to be coated is required to have a film thickness which allows the minus electricity to pass through and which prevents the plus electricity from passing through in a kilohertz region. Thus, usually a thin film of 1 nm to 500 nm is used although there is a difference depending on which of a polycrystalline thin film, an amorphous thin film, and a monocrystalline thin film is used. Since the outer side of the p-type semiconductor film 9 is subjected to friction, a film thickness of 50 nm is preferable; however, for the n-type semiconductor film 8, a film thickness of about 1 nm may be used.

For the n-type semiconductor film 8 and the p-type semiconductor film 9, for example, different kinds of semiconductors, such as silicon and gallium phosphide, may be used, respectively. However, since a p-n junction forms a heterojunction, it is desirable to use the same kind of semiconductor so that the movement of electrons is smooth. In an example of a bonding state of the semiconductors shown in FIG. 4, the p-type semiconductor film 9 of the composite medial treating device 10 is formed of a boron-doped silicon. Silicon Si is given with a valence of four and has four bonding electrons 17 to form a diamond bonding. However, since boron B contained therein is given with a valence of three and has three bonding electrons 20, holes 21 are produced. On the other hand, the n-type semiconductor film 8 which is in contact with the p-type semiconductor film 9 is formed of an antimony-doped silicon. Since antimony-doped Sb in the silicon Si is given with a valence of five and has five electrons 18, one of the five electrons 18 is an excess electron 19. This excess electron 19 moves to the hole 21 in the p-type semiconductor film 9 and is stabilized. As a result, the n-type semiconductor film 8 is charged to plus potential, and the p-type semiconductor film 9 is charged to minus potential. The p-type semiconductor film 9 also has the effect of maintaining the epidermis 2 to minus potential, due to contact of the epidermis with minus potential of the p-type semiconductor film 9. In this case, when the ferrodielectric substance 7 is of the n-type as is the case in titanium oxide, the same effect will be obtained by omitting the n-type semiconductor film 8, and a p-type semiconductor film 9 is grown directly on the ferrodielectric substance 7.

For the n-type semiconductor film 8 and the p-type semiconductor film 9, a thin film of silicon, germanium, gallium phosphide, indium phosphide, zinc selenide, zinc sulfide, or an organic semiconductor may be used. However, in view of cost and handling easiness, a thin film of the silicon germanium, or the organic semiconductor is frequently used. In the case of the organic semiconductor, a minus charged one is used as p-type, and a plus charged one is used as n-type.

Figure 6:
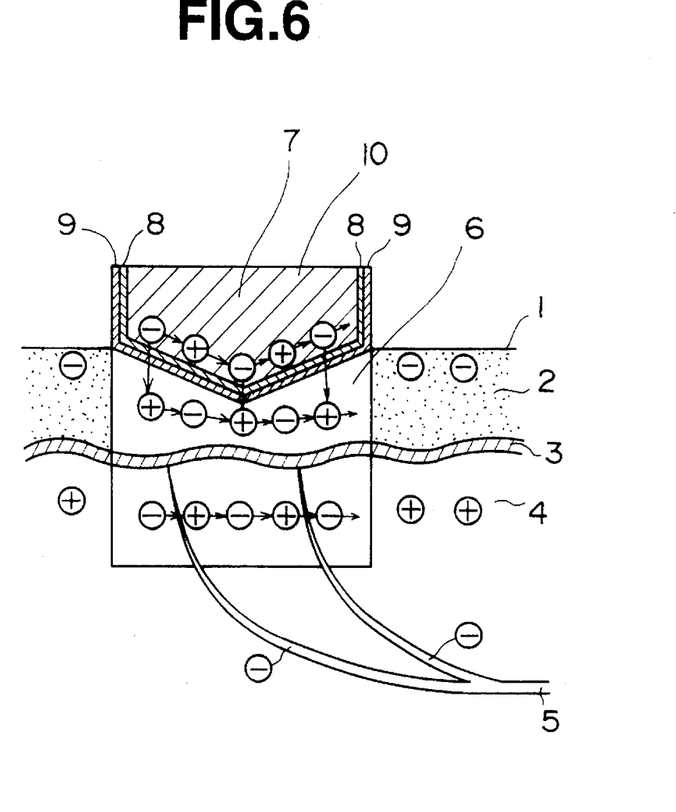
FIG. 6 is a diagram for explaining a state in which a composite medical treating device is affixed to skin having a stiff portion and a pain.

With reference to FIG. 5, when the human body feels a stiff portion or a pain, in a part 6 having the stiff portion or pain, a dermis potential fluctuates between −, +, −, +, −. In response to this fluctuation of the dermis potential, the potential of the epidermis 2 fluctuates between +, −, +, −, +. Accordingly, as shown in FIG. 6, when a composite medical treating device 10 composed of a ferrodielectric substance 7 and a semiconductor is affixed to the part 6 having the stiff portion or pain as shown in FIG. 5, in response to the changes of the epidermis potential between +, −, +, −, +, potentials −, +, −, +, − of opposite phase to that of the epidermis potentials are induced in a surface of the ferrodielectric substance 7. However, since laminations of the n-type semiconductor film 8 and the p=type semiconductor film 9 are coated on the surface of the ferrodielectric substance 7, because of the properties of the semiconductor, minus electricity is allowed to flow through the n-p laminations (n-p semiconductor junction) to the epidermis 2. However, plus electricity does not pass through the n-p laminations and does not flow to the epidermis 2. Accordingly, the composite medical treating device 10 allows only the minus electricity to flow to the epidermis 2, and maintains such stimulus during a period in which the potential at the part 6 having the stiff portion and pain is swinging.

Figure 7:
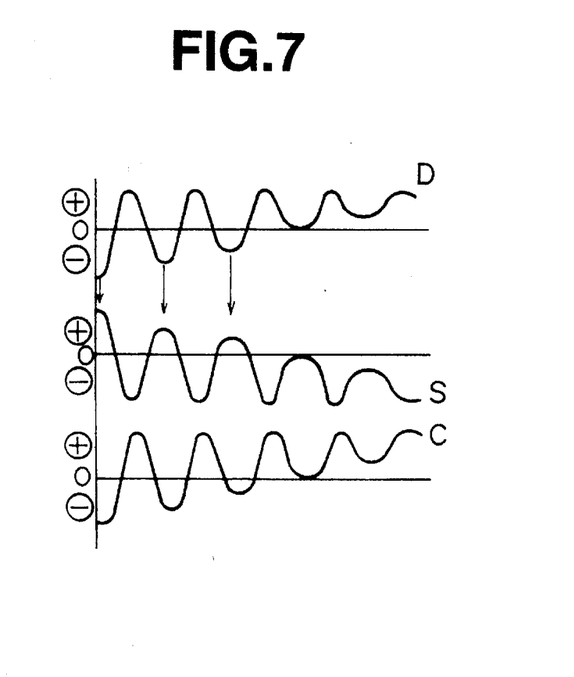
FIG. 7 is a graph showing changes of a potential in skin and a surface potential of a ferrodielectric substance when a composite medical treating device is affixed to the skin.
Figure 8:
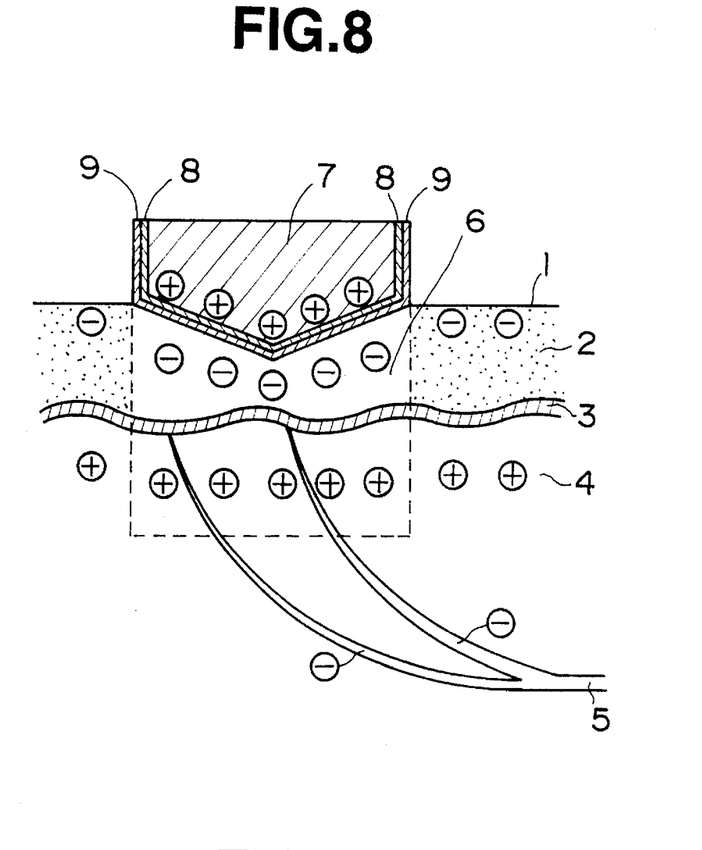
FIG. 8 is a diagram for explaining a state in which the stiff portion and the pain are removed after the composite medical treating device is affixed to the skin.
Figure 9:
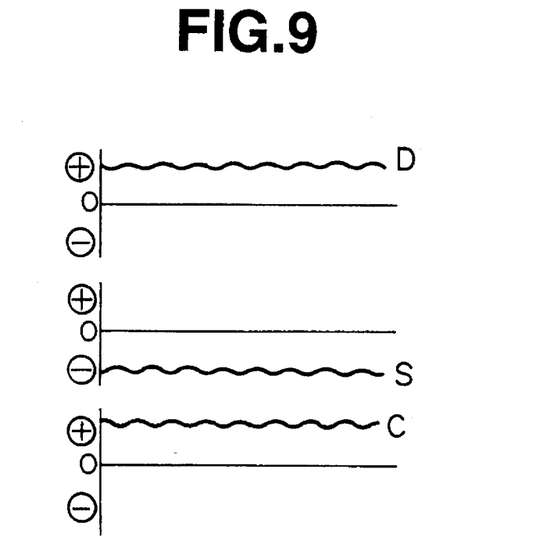
FIG. 9 is a graph showing changes of the potential in the skin and the surface potential of the ferrodielectric substance when the stiff portion and the pain are removed.

As shown in FIG. 7, when the epidermis potential S returns from plus to minus, the dermis potential C returns to plus and is stabilized due to the dielectric action. Thus, the injection of $Na^+$ ions into the nerve is also suppressed and the pain is reduced. Ultimately, a stabilized state as shown in FIGS. 8 and 9 is achieved, and the part 6 is released from the stiff portion and pain. Once the pain is removed, the surface potential D of the ferrodielectric substance becomes plus and, since minus potential is not generated, minus electricity does not excessively flow to the epidermis 2 resulting in a safe condition.

EXAMPLE 1

12 g of barium titanate, 50 g of epoxy resin, and 20 g of a curing agent are added to form a coating material, and the coating material is coated on cotton cloth having a width of 150 mm and a length of 230 mm. After curing and drying, an n-type silicon semiconductor doped with phosphorous of 200 ppm is sputtered to a thickness of 50 nm, and thereon a p-type silicon semiconductor doped with boron of 200 ppm is sputtered to a thickness of 100 nm. The coated cloth is then cut to obtain a disk-shaped sample having a diameter of 15 mm.

As a comparative example, 12 g of barium titanate, 50 g of epoxy resin, and 20 g of a curing agent are added to form a coating material, and the coating material is coated on cotton cloth, and then cured and dried. In this case, semiconductor thin films are not coated.

First, samples of the comparative example were affixed on four to ten positions of oppressive pain portions of twelve patients having a stiff shoulder. After three days, one patient showed favorable progress, four patients showed somewhat favorable progress, and seven patients showed no change. Then, the samples of the comparative example were removed, and after one hour, samples of the example 1 were affixed to the same positions of eleven patients including the four patients who showed somewhat favorable progress and the seven patients who showed no change. After three days, seven patients showed favorable progress, three patients showed somewhat favorable progress, and one patient showed no change. The kinds of the samples used were not disclosed to the patients.

Assuming that the percentage of effectiveness for somewhat favorable progress is 50%, and when the percentage of effectiveness for the patients is simply calculated, it is 25.0% in the comparative example, and in the example 1, it is 77.3% for eleven patients. When one patient showed favorable progress in the comparative example is calculated as also showing favorable progress in the example 1, the percentage of effectiveness for twelve patients becomes 79.2%.

EXAMPLE 2

Silicone resin coating is carried out on cotton cloth having a width of 150 mm and a length of 230 mm, and thereon, a mixture of 12 g of lithium titanate, 50 g of epoxy resin, and 20 g or a curing agent, which mixture is diluted by 50 ml of methyl isobutyl ketone, is coated and then dried and cured. Further, on a surface of the resultant product, an n-type silicon semiconductor doped with phosphorous of 200 ppm is sputtered to a thickness of 80 nm, and thereon, a p-type silicon semiconductor doped with boron of 200 ppm is sputtered to a thickness of 100 nm, and coated thereon, an acrylic adhesive mass is coated twice before the cloth is cut into a disk-like sample having a diameter of 20 mm.

As a comparative example, an n-type silicon semiconductor doped with phosphorous of 200 ppm is sputtered to a thickness of 80 nm on cotton cloth coated with only epoxy resin, and thereon a p-type silicon semiconductor doped with boron of 200 ppm is sputtered to a thickness of 100 nm, and thereon an acrylic adhesive mass is coated twice.

Samples of the comparative example were affixed to four positions on the back of the heads of six patients having a headache due to a hangover. After such affixing, the result is that two patients showed favorable progress, three patients showed somewhat favorable progress, and one patient showed no change.

Samples of example 2 were affixed to the same position on ten patients. After the affixing, the result is that eight patients showed favorable progress, one patient showed somewhat favorable progress, and one patient showed no change.

The percentage of effectiveness was 58% in the comparative example, and it was 85% in the example 2.

EXAMPLE 3

A mixed crystal powder of lead titanate and lead zirconate mixed in the ratio of 1:1 is added with silicon varnish as a binder, and then, powder compression molded to a disk shape having a cone portion shown in FIG. 1 having a diameter of 7 mm and a thickness of 2 mm, and then, sintered at a low temperature of 300° C. The resultant product is used as a substrate, and an n-type silicon semiconductor doped with phosphorous of 200 ppm is sputtered to a thickness of 30 nm, and thereon, a p-type silicon semiconductor doped with boron of 200 ppm is sputtered to a thickness of 100 nm.

As a comparative example, vinyl chloride is molded to the same size as example 3, and an n-type silicon semiconductor doped with phosphorous of 200 ppm is sputtered to a thickness of 30 nm, and thereon a p-type silicon semiconductor doped with boron of 200 ppm is sputtered to a thickness of 100 nm.

Samples of the comparative example were affixed to six to ten positions on the waist of six lumbago patients having an oppressive pain. After three days, two patients showed favorable progress, and two patients showed no change.

Samples of the example 3 were affixed to six to ten positions on the waist of nine lumbago patients having an oppressive pain. After three days, six patients showed favorable progress, two patients showed somewhat favorable progress, and one patient showed no change.

The percentage of effectiveness was 50% in the comparative example, and 77.8% in the example 3.

EXAMPLE 4

A barium titanate powder is added with sufficient vanish as a binder, and then, powder compression molded to a disk shape having a cone portion as shown in FIG. 1 having a diameter of 6 mm and a thickness of 3 mm, and then, sintered at a temperature of 1250° C. The resultant product is used as a substrate, and an n-type germanium semiconductor doped with antimony of 200 ppm is sputtered to a thickness of 30 nm, and thereon, a p-type germanium semiconductor doped with indium of 200 ppm is sputtered to a thickness of 80 nm.

As a comparative example, an aluminum oxide powder is molded in a similar manner as mentioned above, and a semiconductor film is not coated.

Samples of this example 4 and the comparative example are used to investigate the influence on muscular strength.

The muscular strength test is conducted by the following method.

Persons to be tested including ten males and one female are divided into two groups, and samples of this example 4 are affixed to an example group (five males and one female), and samples of the comparative example are affixed to a comparative example group (five males).

The muscular strength to be tested is muscular strength to stretch the knee, and the total of 11 samples are affixed to portions including those portions surrounding the knee and the femoral region.

As the measurement device, an ariel computerized exerciser is used, and the person to be tested sit on a chair. The femoral region is fixed and each person performs physical exercise to bend and stretch the knee.

The measurement device is set to an angular velocity of 240 degrees/second, and the persons to be tested first performs the physical exercise to bend and stretch the knee with their full power for one minute, and then, performs the exercise for one minute after a rest of five minutes, and further, performs the exercise for one minute after a rest of five minutes, to thereby perform a total of three sets of exercise.

The first set of exercise is performed for a warming-up purpose and to make the persons familiar with the measurement, and the samples are not affixed to both for the first set of exercises. The samples are affixed during the rest period just after the first set of exercise.

In measuring the muscular strength, a maximum value for each person to be tested in the three sets is used as a maximum muscular strength, and the percentage of a measurement value of each time in each set with respect to the maximum muscular strength is plotted, and changes are compared.

Figure 11:
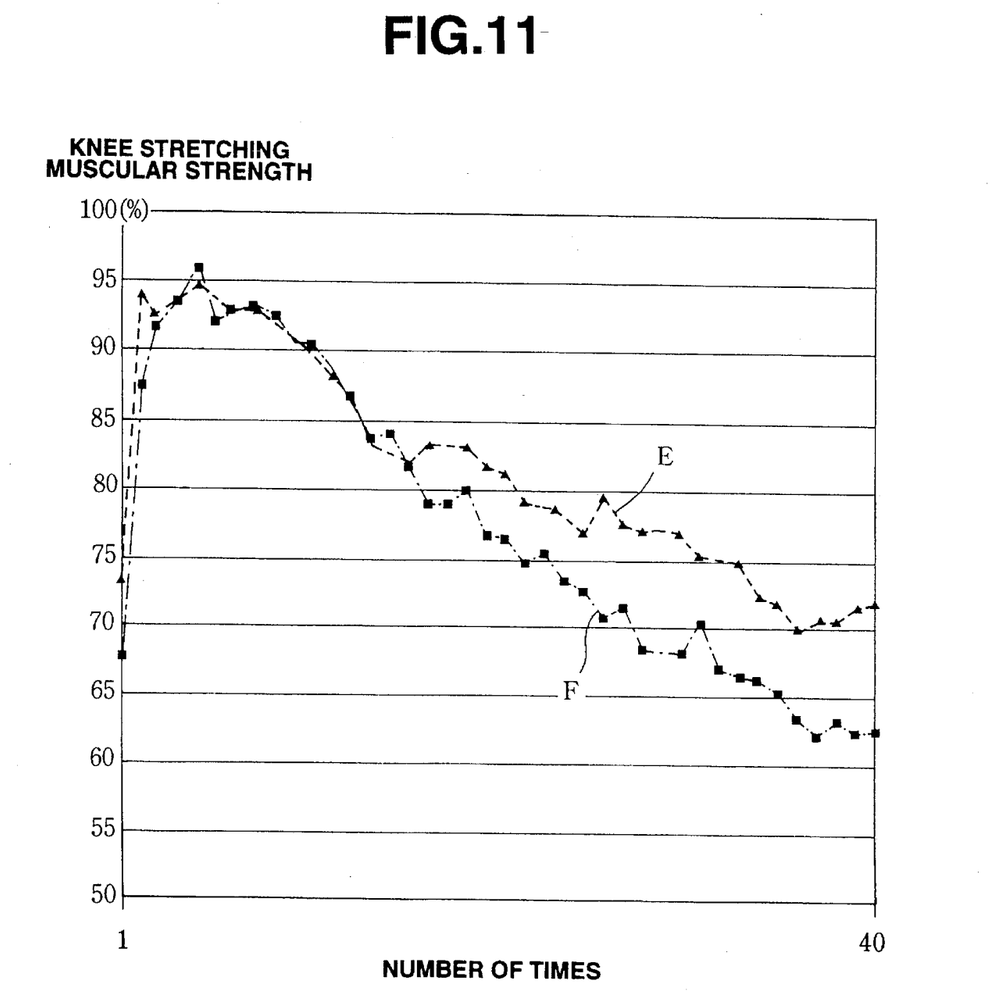
FIG. 11 is a graph showing a change in the knee stretching muscular strength.

In the results of the above-mentioned muscular strength test, the amount of attenuation of the muscular strength of the persons to be tested having the samples of the example 4 affixed thereto becomes smaller than the amount of attenuation of the muscular strength of the persons to be tested having the samples of the comparative example affixed thereto. This trend appeared significantly in the third set. FIG. 11 is a graph showing a change in the knee stretching muscular strength in the third set. In this graph, the ordinate represents the percentage of the maximum muscular strength, the abscissa represents the number of times of bending and stretching the knee, a curve E indicates a means value of six persons in the example group, and a curve F indicates a mean value of five persons in the comparative example group.

Figure 12:
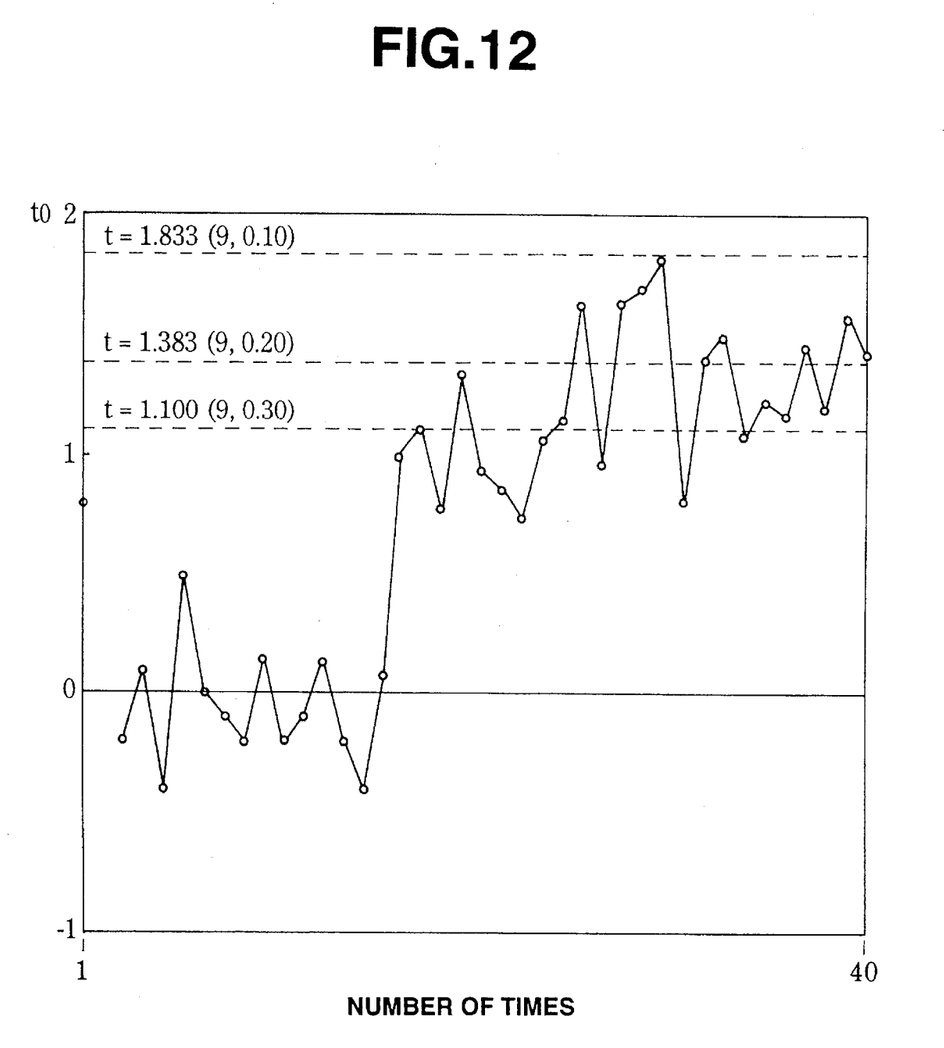
FIG. 12 is a graph showing a result of a test of a significant difference in a muscular strength change between an example group and a comparative example group.

FIG. 12 shows a result of a test (t test) of a significant difference in a muscular strength change between the example group and the comparative example group. From this result, the significant difference is recognized between both groups in the sixteenth time and thereafter in the third set of the knee bending and stretching exercise and, in the example group, muscular fatigue is reduced as compared with the comparative example group. As described above, by affixing the samples of this example 4, since fatigue is reduced, there are effects in the prevention and medical treatment of the pain which is caused as a result of muscular fatigue, and furthermore, in the improvement in athletic ability and sport ability.

As described in the foregoing, in the composite medical treating device composed of a ferrodielectric substance and a semiconductor of the present invention, plus and minus electricity are generated in the ferrodielectric substance in response to a change of a potential of skin at a part having a stiff portion and a pain, and among the plus and minus electricity, only the minus electricity is allowed to flow to the outer skin. As a result, so long as the pain continues, the minus electricity is made of intermittently flow to the outer skin, and it is possible to maintain stimulus and to return the skin to a normal potential. Since this living body reaction utilizes a physiological action of a pain, it is possible to apply it to a wide range, and it is safe since there is no need to invade the living body and/or to hurt the living body.

What is claimed is:

1. A composite medical treating device formed of a ferrodielectric substance and a semiconductor, the device comprising:

one of a ferrodielectric substance and a material containing a ferrodielectric substance; and laminations of an n-type semiconductor film and a p-type semiconductor film coated in this order on the one of the ferrodielectric substance and the material containing the ferrodielectric substance, so that said n-type semiconductor film is in contact with said one of the ferrodielectric substance and the material containing the ferrodielectric substance, and said p-type semiconductor film is in contact with said n-type semiconductor film, and the p-type semiconductor film is affixable to a surface of human skin at a position having a pain, wherein the n-type and p-type semiconductor films provide a stabilization effect to the surface of the human skin at said position.

2. The composite medical treating device according to claim 1, wherein the ferrodielectric substance includes a substance selected from the group consisting of titanium oxide, barium titanate, strontium titanate, lead titanate, lithium niobate, lithium tantalate, PZT, and rochelle salt.

3. The composite medical treating device according to claim 1, wherein the n-type semiconductor film includes a thin film selected from the group consisting of silicon, germanium, gallium phosphide, indium phosphide, zinc selenide, zinc sulfide, and an organic semiconductor.

4. The composite medical treating device according to claim 1, wherein the p-type semiconductor film includes a thin film selected from the group consisting of silicon, germanium, gallium phosphide, indium phosphide, zinc selenide, zinc sulfide, and an organic semiconductor.

5. The composite medical treating device formed of a ferrodielectric substance and a semiconductor, the device comprising:

a material containing a ferrodielectric substance; and laminations of an n-type semiconductor film and a p-type semiconductor film coated on the material containing the ferrodielectric substance, the p-type semiconductor film affixable to a surface of human skin at a position having a pain, wherein the n-type and p-type semiconductor films provide a stabilization effect to the surface of the human skin at said position;

wherein the material containing the ferrodielectric substance is selected from the group consisting of woven textile, and non-woven textile, wherein the ferrodielectric substance is a powder, and wherein the powder is textile blended with the material.

6. A composite medical treating device formed of a ferrodielectric substance and a semiconductor, the device comprising:

a material containing a ferrodielectric substance; and laminations of an n-type semiconductor film and a p-type semiconductor film coated on the material containing the ferrodielectric substance, the p-type semiconductor film affixable to a surface of human skin at a position having a pain, wherein the n-type and p-type semiconductor films provide a stabilization effect to the surface of the human skin at said position;

wherein the material containing the ferrodielectric substance is selected from the group consisting of woven textile, non-woven textile, paper, plastics, and ceramics, wherein the ferrodielectric substance is a powder, and wherein the powder is mixed with the material.

7. A composite medical treating device formed of a ferrodielectric substance and a semiconductor, the device comprising:

a material containing a ferrodielectric substance; and laminations of an n-type semiconductor film and a p-type semiconductor film coated on the material containing the ferrodielectric substance, the p-type semiconductor film affixable to a surface of human skin at a position having a pain, wherein the n-type and p-type semiconductor films provide a stabilization effect to the surface of the human skin at said position;

wherein the material containing the ferrodielectric substance is selected from the group consisting of woven textile, non-woven textile, paper, plastics, and ceramics, wherein the ferrodielectric substance is a powder, and wherein the powder is coated on the material.

8. A composite medical treating device formed of a ferrodielectric substance and a semiconductor, the device comprising:

a material containing a ferrodielectric substance; and laminations of an n-type semiconductor film and a p-type semiconductor film coated on the material containing the ferrodielectric substance, the p-type semiconductor film affixable to a surface of human skin at a position having a pain, wherein the n-type and p-type semiconductor films provide a stabilization effect to the surface of the human skin at said position;

wherein the material containing the ferrodielectric substance is selected from the group consisting of woven textile, non-woven textile, paper, plastics, and ceramics, wherein the ferrodielectric substance is a powder, and wherein the powder is affixed to the material.

* * * * *